United States Patent [19]

Imagawa et al.

[11] Patent Number: 4,684,633

[45] Date of Patent: Aug. 4, 1987

[54] PHOSPHOLIPID-EMULSIFIED PROSTAGLANDIN COMPOSITION

[75] Inventors: Takashi Imagawa, Hyogo; Kazumasa Yokoyama, Osaka; Yutaka Mizushima, Kanagawa, all of Japan

[73] Assignee: The Green Cross Corporation, Osaka, Japan

[21] Appl. No.: 691,023

[22] Filed: Jan. 14, 1985

[30] Foreign Application Priority Data

Jan. 12, 1984 [JP] Japan ................................ 59-3858

[51] Int. Cl.$^4$ ................. A61K 31/685; A61K 31/215; A61K 31/19; A61K 31/557
[52] U.S. Cl. ................................ 514/78; 514/530; 514/938; 514/970; 514/573
[58] Field of Search ................ 514/78, 530, 938, 970, 514/573

[56] References Cited

U.S. PATENT DOCUMENTS

| | | | |
|---|---|---|---|
| 3,598,858 | 8/1971 | Bergstrom et al. | 260/501.15 |
| 4,190,669 | 2/1980 | Voorhees et al. | 424/305 |
| 4,280,996 | 7/1981 | Okamoto et al. | 514/78 |
| 4,563,354 | 1/1986 | Chang et al. | 514/938 |

FOREIGN PATENT DOCUMENTS

| | | |
|---|---|---|
| 0097481 | 6/1983 | European Pat. Off. . |
| 2943885 | 5/1980 | Fed. Rep. of Germany . |
| 0059912 | 4/1983 | Japan ................................ 514/938 |
| 2050799 | 1/1981 | United Kingdom ................ 514/78 |

OTHER PUBLICATIONS

European Search Report.
Chemical Abstracts, vol. 46, No. 5, Mar. 10, 1952, Column 2119(b), Columbus, Ohio, U.S.; D. J. Hanahan et al. & J. Biol. Chem. 192, 623–628, 1951, Abstract.

*Primary Examiner*—Albert T. Meyers
*Assistant Examiner*—John M. Kilcoyne
*Attorney, Agent, or Firm*—Sughrue, Mion, Zinn, Macpeak & Seas

[57] ABSTRACT

A prostaglandin emulsion composition comprising a prostaglandin emulsified with a phosphatidylethanolamine-free phospholipid, the composition being suitable for intravenous administration.

15 Claims, No Drawings

PHOSPHOLIPID-EMULSIFIED PROSTAGLANDIN COMPOSITION

FIELD OF THE INVENTION

This invention relates broadly to phospholipid-emulsified prostaglandin compositions. More particularly, the invention relates to a prostaglandin-containing oil-in-water emulsion emulsified with a phosphatidylethanol-amine-free phospholipid fraction.

BACKGROUND OF THE INVENTION

Prostaglandins are generally known to have pharmacological actions. For example, these compounds have blood pressure lowering and antilipolytic actions, and also inhibit platelet aggregation. Therefore, prostaglandins are of value in the treatment of hypertension, thrombosis, asthma, and gastric and intestinal ulcers, for induction of labor and abortion in pregnant mammals, and for prophylaxis of arteriosclerosis.

Prostaglandins are lipid-soluble substances which are obtainable in very small quantities from various organs of animals which secrete prostaglandins endocrinally. These compounds have biological actions, for example, smooth muscle contracting action on uterine muscle, isolated small intestine, etc., hypotensive or pressor action, antilipolytic action, gastric secretion inhibitory action, central nervous system action, platelet adhesiveness decreasing action, platelet aggregation inhibitory action, antithrombotic action, and stimulant action on epithelial proliferation and keratinization.

Although prostaglandins have these useful properties, prostaglandin compounds present problems due to their chemical instability when they are to be exploited as drugs.

SUMMARY OF THE INVENTION

The intensive research undertaken by the present inventors to overcome the instability of prostaglandins led to the finding that, when they are incorporated into an oil-in-water emulsion, these compounds are not only stabilized but also made adaptable to intravenous administration and that the use of a phospholipid, which is free of phosphatidylethanolamine, as the emulsifier contributes further to the stability of prostaglandins. This invention has been conceived and developed on the basis of the above findings.

Accordingly, this invention provides a prostaglandin emulsion composition comprising a prostaglandin, as the disperse phase, emulsified in water as the continuous phase with phosphatidylethanolamine-free phospholipid.

DETAILED DESCRIPTION OF THE INVENTION

The prostaglandins (hereinafter referred to for brevity as "PG") employed in accordance with this invention include the following compounds and their derivatives.

| Abbreviation | Chemical Name |
| --- | --- |
| $PGF_{2\alpha}$ | (5Z, 13E, 15S)—9α, 11α, 15-trihydroxy-prosta-5,13-dienoic acid |
| $PGE_2$ | (5Z, 13E, 15S)—11α, 15-dihydroxy-9-oxo-prosta-5, 13-dienoic acid |
| $PGD_2$ | (5Z, 13E, 15S)—9α, 15-dihydroxy-11-oxo-prosta-5, 13-dienoic acid |
| $PGF_{1\alpha}$ | (13E, 15S)—9α, 11α, 15-trihydroxy-prost-13-enoic acid |
| $PGE_1$ | (13E, 15S)—11α, 15-dihydroxy-9-oxo-prost-13-enoic acid |
| $PGA_1$ | (13E, 15S)—15-hydroxy-9-oxo-prosta-10, 13-dienoic acid |
| $PGI_2$ | (5Z, 13E, 15S)—11α, 15-dihydroxy-6.9α-epoxy-prosta-5, 13-dienoic acid |
| $PGB_1$ | (13E, 15S)—15-hydroxy-9-oxo-prosta-8(12), 13-dienoic acid |

Preferred examples of these derivatives are the alkyl esters thereof. The alkyl moiety of the alkyl ester of PG can be an alkyl group having 1 to 30 carbon atoms, preferably 1 to 15 carbon atoms and more preferably 3 to 10 carbon atoms. Examples of the alkyl group include a methyl group, an ethyl group, an n-propyl group, an iso-propyl group, an n-butyl group, an iso-butyl group, a tert-butyl group, an n-pentyl group, an n-hexyl group, an n-heptyl group, an n-octyl group, an n-nonyl group and n-decyl group.

The above-described alkyl moiety ($C_{1-30}$ alkyl) may be replaced by a $C_{1-30}$ alkyl—COO—$C_{1-5}$ alkyl group or a $C_{1-30}$—OCO—$C_{1-5}$ alkyl group. Examples of the $C_{1-5}$ alkyl group include a methyl group, an ethyl group, an n-propyl group, an iso-propyl group, an n-butyl group, an iso-butyl group, a tert-butyl group, and an n-pentyl group.

The oil emulsion employed in accordance with this invention is exemplified, predominantly, by those consisting of vegetable oil (for example, soybean oil, cotton seed oil, sesame oil, safflower oil and corn oil), phospholipid and water. The proportions of these components may be such that the oil component accounts for about 5 to about 50 w/v percent, preferably 8 to 30 w/v percent, of the total emulsion and the proportion of the phospholipid component is about 1 to about 5 weight parts, preferably 5 to 30 weight parts, per 100 weight parts of the oil component, the proportion of water being more or less optional. If desired, an auxiliary emulsifier (for example, a fatty acid containing 6 to 22, preferably 12 to 20, carbon atoms or a physiologically acceptable salt thereof (for example, alkalimetal salts such as sodium salts and potassium salts and alkaline earth metal salts such as calcium salts) in a proportion of up to about 0.3% (w/v)), a stabilizer (for example, a cholesterol compound such as cholesterol in a proportion of up to about 0.5% (w/v), preferably up to 0.1% (w/v), or a phosphatidic acid in a proportion of up to about 5% (w/v), preferably up to 1% (w/v) of the total emulsion), a high molecular weight compound (for example, albumin, dextran, vinyl polymers, nonionic surfactants, gelatin, hydroxyethyl-starch, etc., in a proportion of about 0.1 to about 5 weight parts, preferably 0.5 to 1 weight part, relative to 1 weight part of PG), an isotonifying agent (for example, glycerin, glucose, etc.) in a proportion of about 0.1 to 10 w/v percent, preferably 1 to 8 w/v percent and so on may also be employed. While the proportion of PG in the fat emulsion may be adjustable within a certain range depending on the form of the emulsion and the intended use of the final composition, it is generally sufficient to incorporate a very small amount, for example, about 0.2 to 100 μg/ml, of PG in the emulsion.

Referring to the oil component and, for example, to soybean oil, it is a high purity soybean oil. Preferably, a high purity soybean oil (purity: at least 99.9% as triglyceride, diglyceride and monoglyceride) obtainable by subjecting purified soybean oil to further purification by steam distillation is employed.

As the phospholipid, a phospholipid fraction free of phosphatidylethanolamines is employed. Such a phopholipid fraction can be obtained from egg yolk phospholipid and soybean phospholipid fractions, for instance, by subjecting the same to fractionation with an organic solvent in the conventional manner as described, for example, in D. J. Hanahan et al.; *J. Biol. Chem.*, 192, 623–628 (1951) and purifying the same further with the aid of an inorganic adsorbent such as silica gel or alumina. The phospholipid obtainable using such a procedure consists mostly of phosphatidylcholines (about 6 to 80 w/v percent), and may contain other phospholipids such as phosphatidylinositols, phosphatidylserines and sphingomyelin. If sufficient emulsification cannot be accomplished with this emulsifier, an auxiliary emulsifier is employed.

Suitable fatty acids of 6 to 22 carbon atoms described hereinbefore as an example of the auxiliary emulsifier may be those that can be added to and are compatible with drugs. The fatty acid may be straight chain or branched chain, although a straight chain fatty acid such as stearic acid, oleic acid, linolic acid, palmitic acid, linoleic acid, myristic acid, etc., is preferred. The salts thereof are physiologically acceptable salts such as salts with alkali metals (such as sodium, potassium, etc.) and alkaline earth metals (such as calcium).

The stabilizer must be a substance which can be used in pharmaceutical preparations.

The albumin, vinyl polymers and nonionic surfactants which can be used as the high molecular weight compound component are preferably those mentioned below. Thus, as regards albumin, human albumin is desirable from an antigenicity point of view.

Examples of vinyl polymers include polyvinyl pyrrolidone.

Suitable nonionic surfactants include, among others, polyalkylene glycols (for example, polyethylene glycols having an average molecular weight of about 1,000 to about 10,000, preferably 4,000 to 6,000), polyoxyalkylene copolymers (for example, polyoxyethylene-polyoxypropylene copolymers having an average molecular weight of about 1,000 to about 20,000, preferably 6,000 to 10,000), hydrogenated castor oil-polyoxyalkylene derivatives (for example, hydrogenated castor oil-polyoxyethylene (40)-ether, (20)-ether and (100)-ether), castor oil-polyoxyalkylene derivatives (for example, castor oil polyoxyethylene (20)-ether, (40)-ether, and (100)-ether) and so on.

The fat emulsion of this invention is prepared, for example, by the following process.

Thus, predetermined amounts of prostaglandin (e.g, PG I$_2$ ester), phospholipid, and, if desired, the above-mentioned additives are mixed with a required amount of soybean oil, and the mixture is heated at 40° to 75° C. to form a solution. A required amount of water is added to the solution, and the mixture is emulsified at 20° to 80° C. by means of a conventional mixer (for example Homomixer) to give a crude emulsion. Stabilizers and isotonifying agents may be added at this stage.

The crude emulsion is then homogenized at 20° to 80° C. by using a homogenizer (for example, a pressure-jet type homogenizer such as Manton-Gaulin type homogenizer or an ultrasonic homogenizer) to obtain a homogenized, extremely fine fat emulsion containing the prostaglandin, which can be administered by intravenous injection. The emulsion has an average particle diameter of 1.0 μm or less, preferably 0.1 to 0.5 μm, and has an excellent stability against heat-sterilization and storage.

When a Manton-Gaulin type homogenizer is used as the homogenizer, for example, the homogenization of crude emulsion is carried out, for example, passing the crude emulsion through the said homogenizer 0 to 2 times at the first-stage pressure of 100 to 150 kg/cm$^2$ and then 5 to 15 times under the second pressure of 400 to 700 kg/cm$^2$.

The phospholipid-free prostaglandin composition can be administered to animals including humans for the purposes for which prostaglandins are generally administered. The present composition is administered non-orally, i.e., parenterally, and preferably by the intravenous route. The generally recommended administration and dosage schedule is about 1 to about 50 μg as PG in a single daily dose by sustained intravenous infusion at the rate of about 0.02 to about 1 ng/kg of body weight/minute.

In the phospholipid-emulsified PG composition according to this invention, the PG has been stabilized and displays its pharmacological actions with greater efficiencies. This feature coupled with its greater focus selectivity allows clinicians to institute a more effective PG therapy than ever before.

Furthermore, the phospholipid-emulsified PG composition according to this invention can be administered by an intravenous route, and since its pharmacological actions and therapeutic efficacies are stable, therapeutic responses are elicited at reduced dosage levels, with a consequently reduced incidence of side effects.

In addition, adverse local reactions which have heretofore been encountered, such as swelling, dull pain, redness, fever, etc., do not occur with the phospholipid-emulsified PG composition of this invention.

The following examples are intended to illustrate the phospholipid-emulsified PG composition of this invention in further detail but are by no means intended to limit the scope of the invention.

EXPERIMENTAL EXAMPLE 1

The intravenous LD$_{50}$ value of the present composition according to Example 1 in rate was not less than 200 ml/kg body weight for a 10% emulsion and not less than 150 m/kg body weight for a 20% emulsion. It was administered by drip infusion at a conventional rate, no hemolytic reactions were encountered at all.

EXPERIMENTAL EXAMPLE 2

In the same manner as in Example 1, various prostaglandins and phosphatidylethanolamine-free phospholipids were used to produce prospholipid-emulsified PG compositions. The formulations of these compositions are shown in Table 1 below. In order to evaluate the stability of PG in the compositions, the above compositions were subjected to high pressure, short time sterilization at 125° C. for 2.2 minutes to determine the percentage remaining of PG. As shown in Table 1 below, the stabilizing effects were determined for various prostaglandins and their esters, with the effects for alkyl esters being particularly remarkable.

The quantitative determination of PG was carried out by the fractional assay method using high performance liquid chromatography and the residual amounts of PG relative to pre-sterilization values were calculated and are shown as percentage remaining.

REFERENCE EXAMPLE 1

In 600 ml of chloroform-methanol (1:1 by volume) was dissolved 100 g of egg yolk phospholipid, followed by addition of 600 g of alumina under stirring. The stirring was continued for 5 minutes, at the end of which time the mixture was suction-filtered through a G4 glass filter. The alumina thus separated was washed with 400 ml of chloroform-methanol (1:1 by volume).

this emulsion had an average particle diameter of 0.2 to $0.4\mu$ and no droplets greater than $1\mu$ were found.

EXAMPLE 3

The procedures of Example 1 were repeated except that 1 mg of $PGE_2$ and 0.2 g of stearic acid were used in place of $PGE_1$ and oleic acid, respectively.

This procedure yielded a very delicate homogeneous $PGE_2$-containing emulsion. The oil droplets of this emulsion had an average particle diameter of 0.2 to $0.4\mu$ and no droplets greater than $1\mu$ were found.

TABLE 1

| Emulsion | Oil Phase (w/v %) | | Water Phase | Emulsifier | (w/v %) | Percentage Residue (%) |
| --- | --- | --- | --- | --- | --- | --- |
| 1 | Soybean oil 20 $PGE_1$ | $1.5 \times 10^{-3}$ | Glycerin Water | Egg yolk phospholipid fraction free of phosphatidylethanolamine* | 3.0 | 83 |
| 2 | Soybean oil 20 Acetoxymethyl $PGE_1$ ester | $1.5 \times 10^{-3}$ | Glycerin Water | Egg yolk phospholipid fraction free of phosphatidylethanolamine* | 4.0 | 93 |
| 3 | Soybean oil 20 $PGF_{2\alpha}$ | $1.5 \times 10^{-3}$ | Glycerin Water | Egg yolk phospholipid fraction free of phosphatidylethanolamine* | 3.0 | 95 |
| 4 | Soybean oil 20 $PGE_2$ | $1.5 \times 10^{-3}$ | Glycerin Water | Egg yolk phospholipid fraction free of phosphatidylethanolamine* | 4.0 | 85 |
| 5 | Soybean oil 20 $PGE_1$ | $1.5 \times 10^{-3}$ | Glycerin Water | Egg yolk phospholipid fraction containing phosphatidylethanolamine** | 4.0 | 52 |

*Phosphatidylethanolamine removed by the procedure of Reference Example 1.
**The starting material used in Reference Example 1.

The filtrate was pooled with the wash, and 200 g of fresh alumina was added to the combined solution with stirring. The stirring was continued for 5 minutes, after which the mixture was suction-filtered through a G4 glass filter. The alumina thus separated was washed with 200 ml of chloroform-methanol (1:1 by volume). The filtrate was pooled with the wash and the combined solution was centrifuged at 10,000 ppm for 10 minutes at a temperature of 4° C. The supernatant was suction-filtered through a $1.0\mu$ millipore filter and the solvent was distilled off, whereupon at least 60 g of phosphatidylethanolamine-free phospholipid was obtained. (The phosphatidylethanolamine content of this fraction was 0.1% by weight or less.)

EXAMPLE 1

Using a homomixer, 30 g of purified soybean oil, 1.5 mg of $PGE_1$ and 0.72 g of oleic acid, 1.5 g of glycerin J.P. (Japanese Pharmacopoeia) and 100 g of distilled water for injection, and 5.4 g of the purified phosphatidylethanolamine-free phospholipid prepared as in Reference Example 1 were mixed and roughly homogenized. Then, using a Manton-Gaulin homogenizer, the crude homogenate was further homogenized for 10 minutes under a total stress of 500 kg/cm². A very delicate homogeneous $PGE_1$-containing emulsion was obtained by the above procedure. The average particle diameter of the oil droplets of this emulsion was 0.2 to $0.4\mu$.

EXAMPLE 2

The procedure of Example 1 was repeated except that 800 $\mu$g of $PGF_{1\alpha}$ and 0.1 g of linolic acid were used in place of $PGE_1$ and oleic acid, respectively.

In this case, a very delicate homogeneous $PGF_{1\alpha}$-containing emulsion was obtained. The oil droplets of While the invention has been described in detail and with reference to specific embodiments thereof, it will be apparent to one skilled in the art that various changes and modifications can be made therein without departing from the spirit and scope thereof.

What is claimed is:

1. A prostaglandin emulsion composition comprising
   (a) 0.2 to 100 $\mu$g/ml of a prostaglandin selected from the group consisting of $PGF_{2\alpha}$, $PGE_2$, $PGD_2$, PGFHd 1$\alpha$, $PGE_1$, $PGA_1$, $PGI_2$, $PGB_1$ and alkyl esters thereof having 1 to 30 carbon atoms;
   (b) about 5 to 50 w/v percent of a vegetable oil selected from the group consisting of soybean oil, cotton seed oil, sesame oil, safflower oil and corn oil;
   (c) a phosphatidylethanolamine-free phospholipid consisting mostly of phosphatidylcholines being about 1 to about 50 parts per 100 parts of said oil (b); and
   (d) a balance of water;
   and having an average particle diameter of 1 $\mu$m or less.

2. The composition according to claim 1, wherein the proportion of the oil is 8 to 30 w/v percent of the total emulsion.

3. The composition according to claim 1, wherein the proportion of said phospholipid is 5 to 30 parts per 100 parts of said oil (b).

4. The composition according to claim 1, wherein said composition contains 0 to about 0.3 w/v percent of a fatty acid having 6 to 22 carbon atoms or a physiologically acceptable salt thereof as an auxiliary emulsifier.

5. The composition according to claim 4, wherein said fatty acid has 12 to 20 carbon atoms.

6. The composition according to claim 5, wherein the fatty acid is a member selected from the group consisting of stearic acid, oleic acid, linolic acid, palmitic acid, linoleic acid and myristic acid.

7. The composition according to claim 1, wherein said composition contains 0 to 0.5 w/v percent of a cholesterol compound as a stabilizer.

8. The composition according to claim 7, wherein said cholesterol compound is present in a proportion of 0 to 0.1 w/v percent.

9. The composition according to claim 1, wherein said composition further contains one member selected from the group consisting of human albumin, dextran, polyvinylpyrrolidone, a non-ionic surfactant selected from the group consisting of polyalkylene glycols, polyoxyalkylene copolymers, hydrogenated castor oil-polyoxyalkylene derivatives and castor oil-polyoxyalkylene derivatives, gelatin and hydroxyethyl-starch in a proportion of 0.1 to 5 weight parts relative to 1 weight part of prostaglandin in the composition as a high molecular compound.

10. The composition according to claim 9, wherein the proportion of said member is 0.5 to 1 weight part relative to 1 weight part of prostaglandin in the composition.

11. The composition according to claim 9, wherein said polyalkylene glycols have an average molecular weight of about 1,000 to about 10,000, said polyoxyalkylene copolymers have an average molecular weight of about 1,000 to about 20,000, said hydrogenated castor oil-polyoxyalkylene derivatives are selected from the group consisting of hydrogenated castor oil-polyoxyethylene (40)-ether, (20)-ether and (100)-ether, and said castor oil-polyoxyalkylene derivatives are selected from the group consisting of castor oil-polyoxyethylene (20)-ether, (40)-ether and (100)-ether.

12. The composition according to claim 1, wherein the composition further contains glycerin or glucose in a proportion of about 0.1 to 10 w/v percent, as an isotonifying agent.

13. The composition according to claim 1, wherein said oil is a high purity soybean oil having a purity of at least 99.9% as tri-, di-, and mono-glyceride.

14. The composition according to claim 1, wherein said phosphatidylethanolamine-free phospholipid consists of about 6 to 8 w/v percent of phosphatidylcholines and optionally phospholipids selected from the group consisting of phosphatidylinositols, phosphatidylserines and sphingomyelin, and 0 to 0.1 w/w percent of phosphatidylethanolamine.

15. The composition according to claim 1, wherein the composition has an average particle diameter of 0.1 to 0.5 μm.

* * * * *

UNITED STATES PATENT AND TRADEMARK OFFICE
CERTIFICATE OF CORRECTION

PATENT NO. : 4,684,633

DATED : August 4, 1987

INVENTOR(S) : Takashi Imagawa, Kazumasa Yokoyama and Yutaka Mizushima

It is certified that error appears in the above-identified patent and that said Letters Patent is hereby corrected as shown below:

ON THE TITLE PAGE, ITEM [73] should read

-- [73] Assignee: The Green Cross Corporation and

Taisho Pharmaceutical Co., Ltd. --.

Signed and Sealed this

Fifth Day of January, 1988

Attest:

DONALD J. QUIGG

Attesting Officer

Commissioner of Patents and Trademarks